US012304873B2

(12) United States Patent
Koelbing et al.

(10) Patent No.: US 12,304,873 B2
(45) Date of Patent: May 20, 2025

(54) FUNCTIONALIZED CERAMIC ARTICLE

(71) Applicant: INSTITUT STRAUMANN AG, Basel (CH)

(72) Inventors: Zoe Koelbing, Basel (CH); Philippe Chavanne, Holstein (CH); Sven Simeunovic, Winterthur (CH); Marc Stephan, Lorrach (DE)

(73) Assignee: INSTITUT STRAUMANN AG, Basel (CH)

( * ) Notice: Subject to any disclaimer, the term of this patent is extended or adjusted under 35 U.S.C. 154(b) by 415 days.

(21) Appl. No.: 17/784,402

(22) PCT Filed: Nov. 13, 2020

(86) PCT No.: PCT/EP2020/082132
§ 371 (c)(1),
(2) Date: Dec. 5, 2022

(87) PCT Pub. No.: WO2021/115727
PCT Pub. Date: Jun. 17, 2021

(65) Prior Publication Data
US 2023/0131023 A1      Apr. 27, 2023

(30) Foreign Application Priority Data

Dec. 13, 2019   (EP) .................................... 19215987

(51) Int. Cl.
*B29C 67/00*     (2017.01)
*A61C 13/00*     (2006.01)
(Continued)

(52) U.S. Cl.
CPC ...... *C04B 41/4578* (2013.01); *A61C 13/0019* (2013.01); *A61C 13/0022* (2013.01);
(Continued)

(58) Field of Classification Search
CPC ..... B29C 64/1224; B33Y 10/00; B33Y 70/00; C04B 35/6264; C04B 35/64;
(Continued)

(56) References Cited

U.S. PATENT DOCUMENTS 9,908,819 B1    3/2018  Kollenberg
2005/0023710 A1  2/2005  Brodkin et al.
(Continued)

FOREIGN PATENT DOCUMENTS

WO    WO 2018193306    10/2018

OTHER PUBLICATIONS

PCT International Search Report (w/ English translation) for corresponding PCT Application No. PCT/EP2020/082132, mailed on Feb. 25, 2021, 4 pages.

*Primary Examiner* — Thu Khanh T. Nguyen
(74) *Attorney, Agent, or Firm* — Dority & Manning, P.A.

(57) ABSTRACT

The present invention relates to a method for additive manufacturing of a position sensitive colored ceramic article comprising: a) providing at least one flowable ceramic component; b) forming a green body by sequential deposition of the ceramic component provided in step a) and optionally a support material not intended to be part of the final article; c) position sensitive application of a coloring substance in a solvent to at least a part of the surface of the green body formed in step b), wherein the coloring substance is applied simultaneously to the sequential deposition; d) heat treatment or curing of at least a part of the green body surface obtained in step c); wherein the method steps a)-d) are at least performed once; e) optionally removing the support material from the green body; and f) sintering the green body to obtain the ceramic article; wherein the coloring substance is a dyestuff according to ISO 18451-1:2019 (E). In addition, the present invention relates to a system
(Continued)

adapted to perform the method and a control data set configured, when implemented in an additive manufacturing system, to cause the system to execute the steps of the inventive method.

13 Claims, 4 Drawing Sheets

(51) Int. Cl.
| | |
|---|---|
| A61C 13/08 | (2006.01) |
| A61C 13/083 | (2006.01) |
| A61K 6/802 | (2020.01) |
| A61K 6/818 | (2020.01) |
| A61K 6/82 | (2020.01) |
| A61K 6/824 | (2020.01) |
| B28B 1/00 | (2006.01) |
| B33Y 10/00 | (2015.01) |
| B33Y 70/00 | (2020.01) |
| B33Y 80/00 | (2015.01) |
| C04B 35/626 | (2006.01) |
| C04B 35/64 | (2006.01) |
| C04B 41/00 | (2006.01) |
| C04B 41/45 | (2006.01) |
| C04B 41/50 | (2006.01) |
| C04B 41/86 | (2006.01) |

(52) U.S. Cl.
CPC .......... *A61C 13/082* (2013.01); *A61C 13/083* (2013.01); *A61K 6/802* (2020.01); *A61K 6/818* (2020.01); *A61K 6/82* (2020.01); *A61K 6/824* (2020.01); *B28B 1/001* (2013.01); *B33Y 10/00* (2014.12); *B33Y 70/00* (2014.12); *B33Y 80/00* (2014.12); *C04B 35/6264* (2013.01); *C04B 35/64* (2013.01); *C04B 41/0072* (2013.01); *C04B 41/009* (2013.01); *C04B 41/4535* (2013.01); *C04B 41/5007* (2013.01); *C04B 41/86* (2013.01); *C04B 2235/3217* (2013.01); *C04B 2235/3225* (2013.01); *C04B 2235/3229* (2013.01); *C04B 2235/3244* (2013.01); *C04B 2235/36* (2013.01); *C04B 2235/6026* (2013.01); *C04B 2235/661* (2013.01)

(58) Field of Classification Search
CPC .............. C04B 41/0072; C04B 41/009; C04B 41/4535; C04B 41/4578
See application file for complete search history.

(56) References Cited

U.S. PATENT DOCUMENTS

| | | |
|---|---|---|
| 2010/0029801 A1 | 2/2010 | Moszner et al. |
| 2011/0215507 A1 | 9/2011 | Apel et al. |
| 2012/0308837 A1 | 12/2012 | Schlechtriemen et al. |
| 2014/0183799 A1 | 7/2014 | Fischer et al. |
| 2017/0196666 A1 | 7/2017 | Böhm et al. |
| 2018/0148378 A1 | 5/2018 | Mayr et al. |
| 2018/0206952 A1* | 7/2018 | Korten ............... A61C 13/0013 |
| 2018/0303723 A1* | 10/2018 | Köbel .................. B29C 64/393 |
| 2019/0117521 A1* | 4/2019 | Herrmann ............ A61C 13/083 |

* cited by examiner

FUNCTIONALIZED CERAMIC ARTICLE

This application is a national phase application of International Patent Application No. PCT/EP2020/082132, filed Nov. 13, 2020, which, in turn, claims the priority of European Patent Application No. 19215987.9, filed Dec. 13, 2019, both of which are hereby incorporated herein by reference in their entirety.

The present invention relates to a method for additive manufacturing of a position sensitive colored ceramic article comprising:
  a) providing at least one flowable ceramic component;
  b) forming a green body by sequential deposition of the ceramic component provided in step a) and optionally a support material not intended to be part of the final article;
  c) position sensitive application of a coloring substance in a solvent to at least a part of the surface of the green body formed in step b), wherein the coloring substance is applied simultaneously to the sequential deposition;
  d) heat treatment or curing of at least a part of the green body surface obtained in step c);
  wherein the method steps a)-d) are at least performed once;
  e) optionally removing the support material from the green body; and
  f) sintering the green body to obtain the ceramic article;
  wherein the coloring substance is a dyestuff according to ISO 18451-1:2019(E). In addition, the present invention relates to a system adapted to perform the method and a control data set configured, when implemented in an additive manufacturing system, to cause the system to execute the steps of the inventive method.

Additive Manufacturing evolved in the last decades in an industrial applicable technique and is usually used to construct physical objects, particularly prototype parts or small volume manufactured components with complex geometries. Additive Manufacturing systems are based on a computer numerically controlled manufacturing technology, wherein a machine uses digital data from a virtual model of the object and deposits or consolidates successive layers of a liquid, a powder, or a sheet material, corresponding to the requirements of the virtual model. The layers are bound together, either by application of physical or chemical means, and the shape of the part is thereby produced. Such generative manufacturing is fast and very flexible, only short set-up times are necessary and the processible design space for complex geometries is larger as compared to traditional subtractive and formative manufacturing. Nevertheless, compared to conventionally processed parts, additive manufacturing is currently less predictable with respect to the physical and chemical properties in the outcome, because the additionally implemented side-conditions, result in different chemical surroundings compared to the non-additive situation. Usually the base material has to be in a formulation that allows extrusion or jetting through a nozzle and direct sequential consolidation or the base material is conditioned with a separate binder solution. Compared to the conventional techniques, in addition, a different physical treatment is employed, taking at least in part into account the different processing conditions. This situation becomes even more complex in cases, wherein besides manufacturing the inner and outer structure of a physical model also other functional features of the manufactured part are of relevance. The latter might especially be true in cases, wherein the part has to provide a functionalization in the form of inhomogeneous interior or surface properties like different physical strengths, colors, surface features and so on. Such inhomogeneous functionalization is in principle easily achievable thanks to the sequential nature of Additive Manufacturing Systems, but to achieve the required functionalization and, at the same time, assuring the necessary basic quality of the part, is still a major challenge.

In the field of dental ceramic articles, it is even more difficult to achieve an acceptable functionalization, because the quality standards with respect to mechanical stability, aesthetics and safety are very high. Therefore, to date, there have been no commercial 3D printers capable of rapid manufacturing 3D realistic-looking, aesthetic teeth, veneers, or other dental products functionalized in 3 dimensions at economic scale. This finding is largely based on the required variation in color, hardness, and other biological properties within a tooth, and the difficulties of manufacturing close replicas of such complex organic objects.

In the patent literature there can be found several different approaches in the field of functionalization of dental ceramic articles.

US 2010 221 683 A1 for instance discloses a colouring solution for colouring a dental ceramic article, the solution comprising: a solvent and a colouring agent, comprising rare earth element metals or ions being present in the solution in an amount of at least about 0.05 mol/l solvent and transition metals or ions being present in the solution in an amount of about 0.00001 to about 0.05 mol/l solvent. The invention also relates to a process for colouring dental ceramic articles, dental ceramic articles treated either with the colouring solution or obtainable by a process comprising the step of firing the dental ceramic articles.

In addition, WO 00 46 168 A1 discloses the coloration of ceramics by way of ionic or complex-containing solutions. The solutions preferred for this purpose contain defined concentrations of at least one of the salts or complexes of the rare earth elements or of the elements of the subgroups. The invention further relates to a kit that comprises at least one reservoir bottle containing such a coloration solution, a container for the coloration and optionally a sieve.

Furthermore, DE 10 2013 020 445 B4 discloses a method for applying color in the field of dental technology, the method comprising the steps: generating scan data by means of detecting the dental prosthesis using a scanner; computing an image of the dental prosthesis from the scan data by means of a computing unit; displaying the image by means of a display device, wherein the image is displayed as colored with a tooth color; receiving a user input by means of the computing unit; in response to the user input: a) applying the tooth color by means of a color application device onto the dental prosthesis or onto a carrier foil for the dental prosthesis, or b) displaying the image by means of a display device, wherein the image is displayed as colored with a different tooth color, and receiving a further user input, wherein in response to the further user input, an application of the altered tooth color by means of a color application device onto the dental prosthesis, or onto the carrier foil for the dental prosthesis takes place.

Nevertheless, besides the existing solutions in the field of functionalization of dental ceramic articles in the form of coloring dental ceramic articles, there still exists the need for further methods, being able to deliver high quality dental ceramics within the boundaries of an additive manufacturing process.

Therefore, the present invention has the object of providing an additive manufacturing process for a dental ceramic article, capable of selectively functionalizing the ceramic article in the form of providing a natural looking color to the dental ceramic article and, at the same time, keeping the quality and especially the mechanical properties of the functionalized article in the same range compared to a traditional un-functionalized dental ceramic article. In addition, it is an object of the present invent to provide a system, capable of performing the inventive method and a control data set, configured, when implemented in an additive manufacturing system, to cause the system to execute the steps of the inventive method.

Accordingly, the inventive method is a method for additive manufacturing of a position sensitive colored dental ceramic article comprising: a) providing at least one flowable ceramic component; b) forming a green body by sequential deposition of the ceramic component provided in step a) and optionally a support material not intended to be part of the final article; c) position sensitive application of a coloring substance in a solvent to at least a part of the surface of the green body formed in step b), wherein the coloring substance is applied simultaneously to the sequential deposition; d) heat treatment or curing of at least a part of the green body surface obtained in step c); wherein the method steps a)-d) are at least performed once; e) optionally removing the support material from the green body; and f) sintering the green body to obtain the ceramic article, wherein the coloring substance is a dyestuff according to ISO 18451-1: 2019(E).

Surprisingly, it was found that above described method is able to provide highly functionalized dental ceramic articles, wherein the dental article is position sensitive functionalized. The functionalization of the dental article in the form of a coloring yields very precise color schemes and natural looking dental articles are obtainable, for instance comprising color gradation in more than one direction. It is possible to obtain articles, comprising a color gradation throughout the volume of the article in two or more directions. Furthermore, articles are obtainable comprising a specific spot coloring and a smooth color gradation to un-colored areas. The color of the article can therefore show a more detailed and, consequently, more natural looking color tone, also including complex color schemes. Such result and functionalization of e.g. zirconia cannot be obtained through manual application, because manual application has limitations regarding an achievable gradient. For example, color application by brushing cannot lead to seamless coloring gradients throughout the whole volume of the dental piece. In addition, functionalized state of the art dental articles comprise the disadvantage to just offer one color. Therefore, the dental piece milled out of the disks is subject to the same features. Within this background recent products comprising a coloring gradient spanning the height of the disks but fail to establish the same gradient in perpendicular direction. Furthermore, the results according to the invention are achievable by utilizing very small amounts of dyestuffs, only, resulting in a cost-efficient process. Based on the precise control of the required amounts and the position it is further possible to manufacture dental articles, wherein the mechanical stability of the dental article is very similar to the non-functionalized dental article. The overall sinter process is better controlled and more efficient, based on the homogeneous and less disturbed ceramic matrix compared to completely soaking a green body with a dyestuff-solution.

The inventive method is a method for additive manufacturing of a position sensitive colored dental ceramic article. An additive manufacturing process is a process, wherein the formed product is not formed at once, but by sequential deposition of material. A known process type is for instance 3D—printing process, wherein the article or object is formed from a digital model, usually by successively adding material layer by layer. Such processing is different to conventional subtractive and formative manufacturing in the form of machining, casting and forging processes, wherein material is removed from a stock item or poured into a mold and shaped by means of dies or presses. The term additive manufacturing covers a variety of processes in which solutions, dispersions or powder grains being fused together to create the article. FDM, dispersion jetting or powder bed based processes are special types of additive manufacturing techniques. By this additive process a dental article or dental ceramic is created. A dental article is an object directed to replace or create biocompatible, mechanically stable and aesthetic dental restorations, such as crowns, bridges, and veneers. The formed article is a position sensitive colored dental ceramic article. This means, that the article comprises regions comprising a different color compared to other regions of the ceramic article. Especially, it is meant that the article can contain color gradients throughout its full volume and not only close to the surface, as e.g. being achieved by fully soaking the article in a dye solution.

In method step a) at least one flowable ceramic component is provided. The flowable ceramic component can, for instance, comprise glass-based systems mainly comprising silica, glass-based systems mainly comprising silica with fillers, crystalline-based systems mainly comprising alumina with glass fillers or polycrystalline solids based on alumina and zirconia. The ceramic component is flowable in cases, wherein the component can be jetted through a printhead or extruded by force through a nozzle. This can typically be the case, when the component is in a powder, a dispersed or a dissolved or dispersed form. Typically, the ceramic component can be in a crystalline form, wherein the crystalline phases can for instance be leucite, leucite and fluorapatite, lithium disilicate, alumina, spinel, alumina-zirconia, zirconia/fluorapatite-leucite glass-ceramic, sanidine or mixtures thereof. As outlined above, the ceramic component may also be formed from or include high-strength oxides of the elements of the main groups II, III and IV and the subgroups III and IV as well as their mixtures, in particular $Al_2O_3$, $ZrO_2$, both partly and also fully stabilized, MgO, $TiO_2$ and their mixtures. The flowable ceramic component may further include or comprise cross-linkable components, binders, thixotropy agents, buffers, pigments, or other components suitable for being incorporated into a flowable ceramic component.

In method step b) a green body is formed by sequential deposition of the ceramic component provided in step a) and optionally a support material not intended to be part of the final article. Within the additive manufacturing more than one material may be sequentially deposited. One material, the ceramic component, is intended to form the dental article. Another material may be sequentially deposited, wherein this material is not intended to form a part of the final dental article. This material, the support material is intended to mechanically stabilize the deposition of the ceramic component and/or to protect already deposited regions of the part from overheating during the build process by building a support structure around the ceramic component. By using such additional material, more sophisticated structures or models can be generated by deposition. The support material, if necessary, may be removed from the deposited ceramic component by mechanical or other means. The removal of the support material is usually performed prior to the sintering process.

In method step c) a coloring substance in a solvent is position sensitive applied to at least a part of the surface of the green body formed in step b), wherein the coloring substance can be applied simultaneously to the sequential deposition, wherein the coloring substance is a dyestuff according to ISO 18451-1:2019(E). For coloring of the dental article within the additive manufacturing process dyestuffs are used. Dyestuffs according to ISO 18451-1:2019(E) are soluble in the application medium, i.e. dyestuffs differ to pigments, which are usually not or un-soluble in the application medium. Therefore, homogeneous solutions are applied position sensitive on the surface of the article and the solution comprising the dyestuff is able to penetrate at least a part of the article body. The article is a green body, because usually the green body structure has to be physically or chemically altered in order to change the green body into the final article, comprising the required mechanical properties. Position sensitive means, as already explained above, that the application point of the dyestuff can very precisely be chosen based on the spatial resolution of the additive manufacturing method. Position sensitive may mean, that the point of dyestuff application can be chosen within a position accuracy on the green body of less than 100 µm, preferably less than 50 µm and even more preferred of less than 10 µm.

The dyestuff is preferable a metal salt comprising metal cations and organic or inorganic anions. Suitable salts or complexes are preferably those from the group of the rare earths or the 2nd or 8th subgroups, in particular Pr, Er, Fe, Co, Ni, Cu. Salts or complexes with inorganic opposed ions such as e.g. halogens, $SO_4^{2-}$, $SO_3^{2-}$, $NO_2^-$, $NO_3^-$, $ClO_4^-$, $ONC^-$, $SCN^-$, are preferred, which can also mean oxo complexes of acid or basic salts, but not double salts with an element of the 1st or 2nd main groups. Furthermore, salts or complexes with organic ions or ligands are preferred which contain 1 to 30 C atoms and from 1 to 10 heteroatoms, such as O, N, S. In detail, these can be alkoxides or salts of organic acids. Preferred here among the alkoxides are the salts of the C1-C10-alkanols, in particular the methoxides, ethoxides, n- and i-proproxides and n-, i-, sec. or tert.-butoxides. Among the salts of organic acids, those of mono-, di- and tri-C1-C20-carboxylic acids are preferred, in particular formate, acetate, malate, maleate, maleinate, tartate, oxalate. Finally, the ligands are also taken to include complexing agents serving to stabilize the metal salts in their oxidation stage and in solution. These can be organic C2-C20 molecules with up to 10 hetero atoms, O, N or S, including in particular EDTA and its salts, NTA, salicylic acid, phenols, 5-sulphosalicylic acid etc. Aqueous or alcoholic solutions of Pr, Er, Fe, are preferred, for example as chlorides, acetates or alcoholates. The ions or complexes are preferably used in concentrations of 0.0001 to 15 wt.-%, particularly preferably from 0.001 to 10 wt.-% and quite particularly preferably from 0.01 to 10 wt.-%.

In method step d) a heat treatment or curing of at least a part of the green body surface obtained in step c) is performed. In order to increase the structural integrity of the green body the deposited component is subjected to a heat treatment or curing step. The step alters the chemical or physical surrounding in the ceramic component and results in a better cohesion of the layer-wise deposited component. For instance, it is possible to remove a part of the flowable composition comprising the ceramic component, for instance a solvent, to increase the stability. Curing may also include a partial or full cross-linking of cross-linkable components in the ceramic component. A heat treatment for improving the layer cohesion may be performed at a temperature of 50-500° C., preferably between 100-400° C., even more preferred between 150-300° C. for a time interval ranging from 10 milliseconds up to 10 minutes. The heat treatment or the curing may be performed at once for all of the deposited layers or the treatment can for instance be performed during or after deposition of one layer.

Within the inventive method the method steps a)-d) are at least performed once. In order to form the green body by the additive manufacturing process according to the invention the single steps are preferably repeated several times. The number of repetitions is a function of the dental article height, the article design and the layer height of the sequentially deposited ceramic component.

In method step e) the support material is optionally removed from the green body. Before performing the final sintering step, wherein the dental ceramic article is achieved, the support material can be removed from the green body. Based on the partial curing or heating treatment the green body is mechanically stable for further handling. The support material can be removed for instance by brushing or blowing. In addition, it is possible to remove the support material by a solvent treatment, wherein the support material is either dissolved or washed away.

In method step f) the green body is sintered to obtain the ceramic article. In order to transform the green body to the desired dental article, the green body is subjected to a heat sintering treatment. Within this treatment the physical and chemical structure of the green body is changed and the mechanical stability of the article is enhanced. Within this treatment usually also unwanted remaining solvents in the green body are removed. The green body is also dried. A suitable time-temperature range for the inventively processed dental ceramic articles may be from 10 minutes up to 40 hours in a temperature range from 700° C.-1500° C.

Within a preferred embodiment of the method the dyestuff may comprise a solubility in the solvent of step c) at 20° C. of ≥0.1 g/l and ≤100.0 g/l. In order to achieve a very natural color gradient and a very even penetration of the dyestuff into the ceramic component, it has been found useful, that the dyestuff solubility is in the above given range. It is possible to achieve a very precise gradation and, consequently, a very natural color tone is achieved by utilizing dyestuffs comprising this solubility range. Lower solubilities can be disadvantageous, because too high solvent volumes may be necessary to apply the necessary dyestuff concentration.

Within a preferred embodiment of the method the flowable ceramic component can be sequentially deposited in the form of particles dispersed in a dispersion medium. It has been found favorable, that the ceramic component is deposited in the form of a dispersion in a dispersion medium. Such deposition of a dispersion may increase the deposition homogeneity and may further increase the position sensitivity of the dyestuff application. Without being bound by the theory, it is believed that in contrast to a ceramic powder the additional dispersion medium limits the diffusion of the dyestuff. Therefore, the additionally applied dyestuff penetrates the ceramic component less quickly, compared to a pure ceramic powder deposition. Finer and more pronounced details can be achieved by using a ceramic component dispersion.

Within a preferred embodiment of the method the dispersion medium can be selected from the group consisting of water, ethanol, methanol, propanol, glycol derivates, butoxyethoxyethanol, butoxyethoxymethanol or mixtures of at least two components thereof. This group of dispersion media for the ceramic component has been found useful for achieving very homogeneous green bodies. In addition, the components are non-toxic and can easily be removed, at least in part, in the course of the heating/curing treatment. In addition, in the sintering process these solvents can be burned without forming unwanted or even toxic thermal degradation products.

Within a preferred aspect of the method the particles can be selected from the group consisting of zirconium oxide, hafnium oxide, yttrium oxide, cerium oxide, aluminum oxide, or mixtures of at least two components thereof. These particles can advantageously form a part or the complete ceramic component and these oxides can be homogeneously dispersed in the above given group of dispersion media. Highly homogenous green bodies and sintered dental articles are obtainable and, in addition, by utilizing this group of ceramic components highly natural looking and mechanically stable dental articles can be formed.

In another preferred characteristic of the method the dispersion medium may comprise a water content of $\geq 50$ wt. % and $\leq 100$ wt. %. For achieving a highly position sensitive coloration it has been found beneficial, to use an aqueous dispersion for the layer-wise deposition of the ceramic component. Within the above given range, the viscosity of the dispersion is low enough to achieve highly homogeneous green bodies. In addition, water as the dispersion medium seems to be very favorable for limiting the dyestuff diffusion capabilities, resulting in a high spatial resolution for the dyestuff application.

In another preferred characteristic of the method the dispersion medium may comprise $\geq 10$ wt. % and $\leq 40$ wt. % 2-(2-Butoxyethoxy)ethanol; and the dispersed particles may comprise $\geq 30$ wt. % and $\leq 60$ wt. % zirconium oxide, $\geq 0,001$ wt. % and $\leq 3$ wt. % hafnium oxide, $\geq 0.001$ wt. % and $\leq 8$% yttrium oxide. This combination of dispersion medium and ceramic component composition is able to result is very stable green bodies and dental ceramic articles and, in addition, this dispersion composition can efficiently and very precisely be colored by the dyestuffs according to the invention.

In a further preferred embodiment of the method the dispersed particles may comprise $\geq 2$ wt. % and $\leq 10$ wt. % yttrium oxide, $\geq 0,001$ wt. % and $\leq 10$ wt. % hafnium oxide, $\geq 0.001$ wt. % and $\leq 3$ wt. % aluminum oxide. This ceramic component composition is able to result is very stable green bodies and dental ceramic articles and, in addition, this composition can efficiently and very precisely be colored by the dyestuffs according to the invention.

Within a further preferred aspect of the method the particles can be selected from the group consisting of silica-based glasses or mixtures thereof. These particles can advantageously form a part or the complete ceramic component and especially silica-based glasses can be homogeneously dispersed in the above given group of dispersion media. Highly homogenous green bodies and sintered dental articles are obtainable and, in addition, by utilizing this group of ceramic component highly natural looking and mechanically stable dental articles can be formed. Silica-based glasses mainly comprise silicon-dioxide and the glass may comprise a fully amorphous or partially crystalline structures. The silica-based glass may also comprise other structural units besides silicon dioxide. Further structural units may be selected from the group consisting of boron trioxide ($B_2O_3$), aluminum oxide ($Al_2O_3$) or phosphorous (oxides). Therefore, useful silica-based glasses can be selected from the group consisting of silica glasses, borosilicate glasses, aluminosilicate glasses, phosphorous-silicate-glasses or mixtures thereof. In addition, these glasses may further comprise zirconium oxide, hafnium oxide, yttrium oxide, cerium oxide. A typical content of the further structural units can be in the range of 5-20 weight-%. The pure silica-based glasses or the further mentioned silica-based glass-types comprising further structural units are preferably glass-ceramic materials containing non-crystalline glass and crystalline ceramic phases.

In another preferred aspect of the method the dispersion medium is at least partially evaporated during step b) and/or d). In order to provide a homogeneous chemical and physical surrounding for position sensitive application of the dyestuff, it has been found useful to remove at least a part of the dispersion medium prior to dyestuff application. This step might increase the position reproducibility and the color tone, probably by leveling the dyestuff penetration depth and hence also the dyestuff surface concentration.

In another preferred aspect of the method the heating or curing step d) can be performed position sensitive. Besides heating or curing large green body areas it has been found useful to apply also the heating or curing as a function of the position on the green body surface. This minimizes the thermal stress on other parts of the green body and energy can be saved. A position sensitive heating or curing may be achieved, when the heating or curing is limited to a certain surface area only. Suitable surfaces areas may range from 10 $\mu m^2$ up to 1000 $\mu m^2$, preferably from 50 $\mu m^2$ up to 500 $\mu m^2$.

In another preferred embodiment of the method the heating or curing step d) may also comprise a levelling treatment of the dried layer. In order to achieve a homogeneous sequential deposition of the ceramic component it has been found useful to also include a levelling treatment in the heating or curing step. The levelling may be achieved by a controlled ablation of the outer surface of the deposited layer. In consequence, the next layer can be deposited on a very even surface. This might increase the homogeneity of the green body and may also increase the position sensitivity of the dyestuff application, because the dyestuff can be applied on a very defined surface comprising a very defined surface roughness. The levelling may for instance be performed by a laser, rasp or by a grater.

In another preferred embodiment of the method the coloring substance may comprise a metal salt, wherein the metal salt comprises anions from the group consisting of $Cl^-$, $OAc^-$, $NO_3^-$, $NO_2^-$, $CO_3^{2-}$, $HCO_3^-$, $ONC^-$, $SCN^-$, $SO_4^{2-}$, $SO_3^{2-}$, lactate, fumarate or mixtures of at least two components thereof. In order to achieve a sufficient dissolution of the dyestuff these anions have been found suitable. Preferable anions are the ones based on carbon, hydrogen and oxygen, because these anions ideally leave no residue in the ceramic component after the sintering step. In addition, these anions do not interfere significantly with the ceramic components and do not alter the obtainable mechanical stability of the dental ceramic article.

In a further preferred aspect of the method the coloring substance may comprise a metal salt, wherein the metal salt comprises cations selected from the group consisting of Fe, La, Ce, Pr, Nd, Sm, Eu, Gd, Tb, Dy, Ho, Er, Tm, Yb, Lu, Mn, V, Cr, Ni or mixtures of at least two components thereof. The oxides of the above given group comprise the right solubility in a large group of solvents and the application of these dyestuffs result in natural looking colors in combination with the above described ceramic components and anions.

In a further preferred embodiment of the method the solvent of the coloring substance in step c) can be selected from the group consisting of glycol derivates, water, ethanol, methanol, propanol, butanol, butoxyethoxyethanol, butoxyethoxymethanol, tert-butyl methyl ether or mixtures of at least two components thereof. It has been found useful, to dissolve the dyestuff in one or more of above given members of suitable solvents. These solvents are able to dissolve a sufficient amount of dyestuffs and are able to change the color of the ceramic component even by applying small dyestuff volumes, only. The achievable dyestuff viscosity is in the right range and based on the viscosity the position sensitivity of dyestuff application is in the right range, resulting in a defined penetration profile of the dyestuff into the ceramic component.

Furthermore, a functionalized dental ceramic article obtained by the inventive method is within the scope of the invention. The functionalized dental ceramic article is suitable for being inserted into the human mouth and is especially non-toxic. Suitable maximum dimensions of the ceramic article may be in the range of 1 mm to 25 mm, preferable in the range of 5 mm to 15 mm. With respect to the further advantages of the functionalized dental ceramic article it is especially referred to the advantages of the inventive method.

In addition, a system adapted to perform the inventive method is within the scope of the invention. A system according to the invention may comprise for instance three or more printer heads, adapted to deposit position sensitive powders or solutions. The system may further comprise means for a levelling treatment and a position sensitive heating or curing. Furthermore, the system may comprise a moveable support structure and a control system, adapted to control the movement of the printer heads and/or the support structure. The position and the output of the printer heads may be independently and individually controllable by the control system.

In a preferred embodiment of the system the system may comprise means for position sensitive heating or curing of the green body. For achieving a very homogeneous chemically surrounding before the sintering step and in order to minimize the energy input in the system it has been found useful, to limit the heating and curing only to surface regions of the green body where it is necessary. Such position sensitive heating or curing can for instance be achieved by a spot treatment of the green bodies surface. Typical spot diameters may be larger or equal to 50 µm and smaller or equal to 5000 µm, preferably larger or equal to 100 µm and smaller or equal to 1000 µm. The spot treatment may include the irradiation of the spot by a laser or other energy source.

It is further within the scope of the invention to disclose a control data set comprising a plurality of control instructions is within the scope of the invention, wherein the control instructions are configured, when implemented in an additive manufacturing system, to cause the system to execute at least the step of:
b) forming a green body by sequential deposition of a ceramic component and optionally a support material not intended to be part of the final article;
c) position sensitive application of a coloring substance in a solvent to at least a part of the surface of the green body formed in step b), wherein the coloring substance can be applied simultaneously to or after sequential deposition and wherein the coloring substance is a dyestuff according to ISO 18451-1:2019(E);
d) heat treatment or curing of at least a part of the green body surface obtained in step c);
wherein the method steps b)-d) are at least performed once.

The present invention will be further described with reference to the following figures without wishing to be limited by them.

Figure 1:
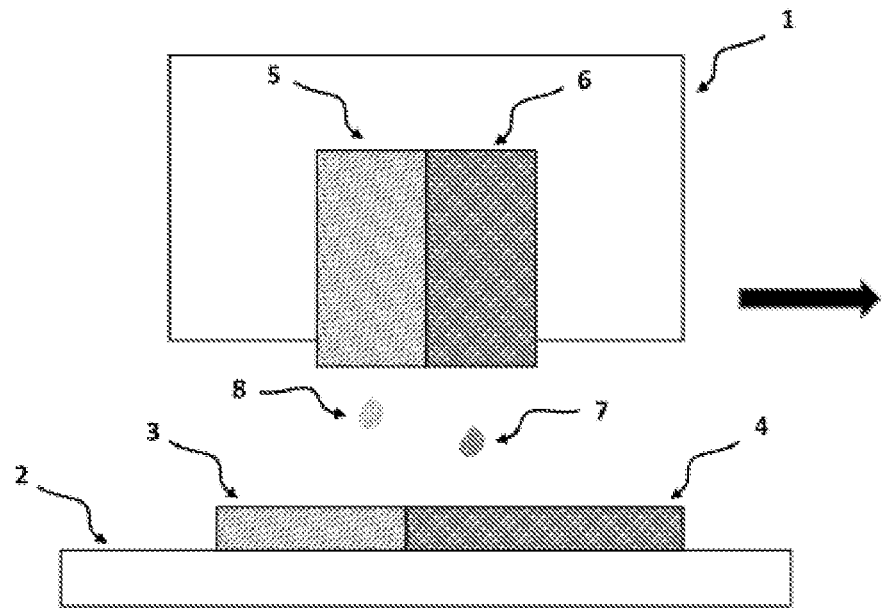
FIG. 1 shows a schematic representation of an additive manufacturing system.

FIG. 1 shows a schematic representation of an additive manufacturing system according to the state of the art. The system comprises a printer head 1 and a support structure 2. The arrow indicates the moving direction either of the printer head 1 or the support structure 2. The additive manufacturing is performed by sequential deposition of a support material 7 and a ceramic component 8 onto the support structure 2. Based on the deposition, regions of support material 4 and regions of the ceramic component 3 can be found either directly on the support structure 2 or on previous deposited layers. The regions of the support material 4 will not be part of the final dental article. These regions are removed before the ceramic component 3, usually designated as green body, is sintered in method step f) to obtain the mechanically functional ceramic article.

Figure 2:
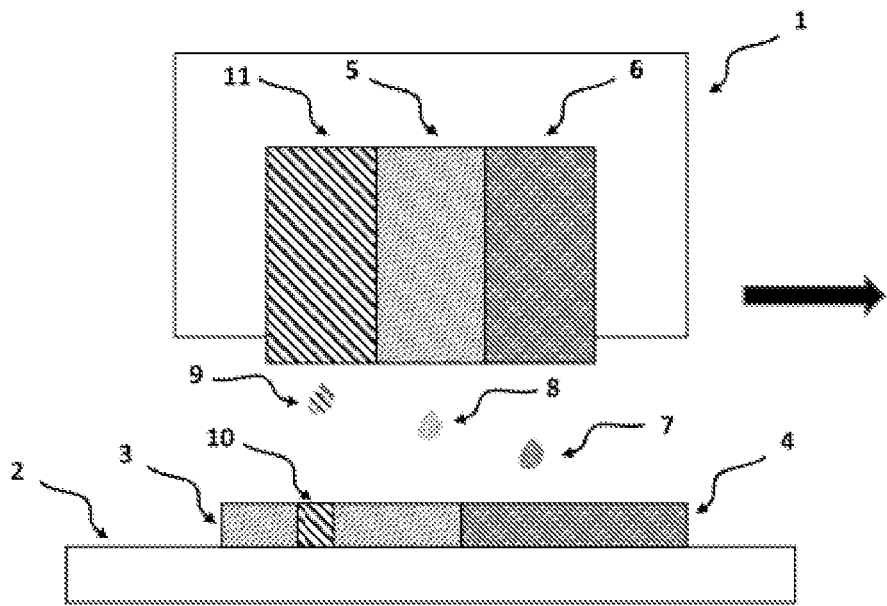
FIG. 2 shows a schematic representation of an additive manufacturing system according to the invention comprising a dyestuff-printer head.

FIG. 2 shows a schematic representation of an additive manufacturing system according to the invention. The system comprises a printer head 1 and the support structure 2. In contrast to the system in FIG. 1 the printer head 1 comprises three different printer heads 5, 6, 11. Besides the printer head for the support material 6 and the printer head for the ceramic component 5 the printer head 1 comprises a printer head 11 for a dyestuff. Consequently, the printer head for the support material 6 deposits the support material 7, thereby forming regions of support material 4; the printer head for the ceramic component 5 deposits the ceramic component 8, thereby forming regions of ceramic component 3. The printer head for the dyestuff 11 deposits the dyestuff 9 onto the regions of the ceramic component 3 and thereby these regions of the ceramic component 3 are altered with respect to the chemical composition. Based on the deposition of the dyestuff 9 the regions of deposited ceramic component 3 are changed in their color. The color change of the regions of ceramic component 3 may be immediately visible or the change may be achieved after an additional physical or chemical treatment of that region 10 such as sintering in method step f). Based on the additive manufacturing process the dyestuff 9 can be placed very position and volume sensitive and allows a very precise tailoring of the color of the dental article. Furthermore, it is possible to achieve color gradients in one or more directions even in difficult geometries of the green body. Such gradation cannot be achieved by other techniques like brushing, dipping or manual application.

Figure 3:
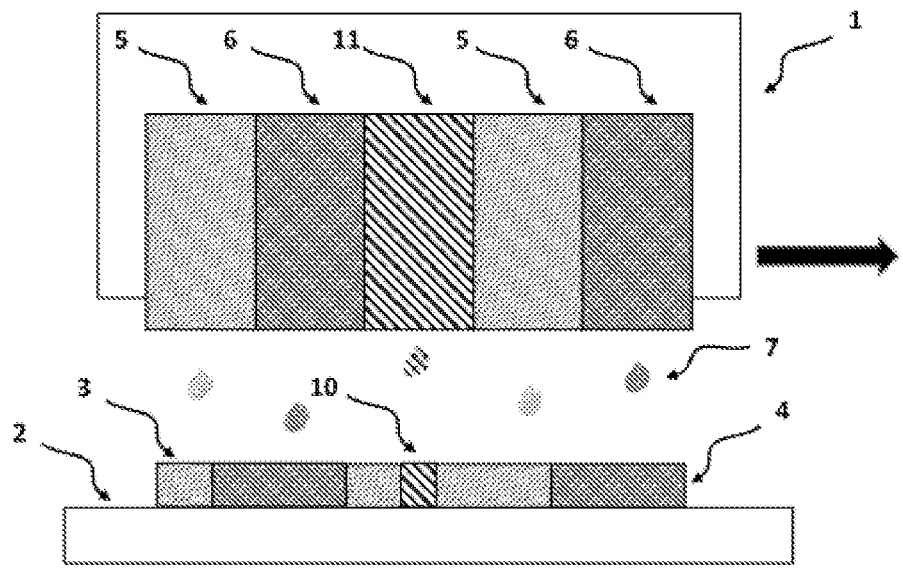
FIG. 3 shows a schematic representation of an additive manufacturing system according to the invention comprising a dyestuff-printer head and a multifold of ceramic component and support structure printer heads.

FIG. 3 shows a schematic representation of an additive manufacturing system according to the invention. In comparison to FIG. 2 this system also comprises a printer head 1 and the support structure 2. In contrast to the system in FIG. 2 the printer head 1 comprises five different printer heads 5, 6, 11. Besides the two printer heads for the support material 6 and the two printer heads for the ceramic component 5 the printer head 1 comprises one printer head 11 for a dyestuff. Consequently, the printer heads for the support material 6 deposit the support material 7, thereby forming regions of support material 4; the printer heads for the ceramic component 5 deposit the ceramic component 8, thereby forming regions of ceramic component 3. The printer head for the dyestuff 11 deposits the dyestuff 9 onto the regions of the ceramic component 3 and thereby these regions of the ceramic component 3 are altered with respect to the chemical composition. Based on the deposition of the dyestuff 9 the regions of deposited ceramic component 3 are changed in their color. The color change of the regions of ceramic component 3 may be immediately visible or the change may be achieved after an additional physical or chemical treatment of that region 10. Based on the additive manufacturing process the dyestuff 9 can be placed very position and volume sensitive and allows a very precise tailoring of the color of the dental article. Furthermore, it is possible to achieve color gradients in one or more directions even in difficult geometries of the green body. The doubling of the printer heads 5 for the ceramic component and the printer heads 6 for the support material enables faster processing speeds.

Figure 4:
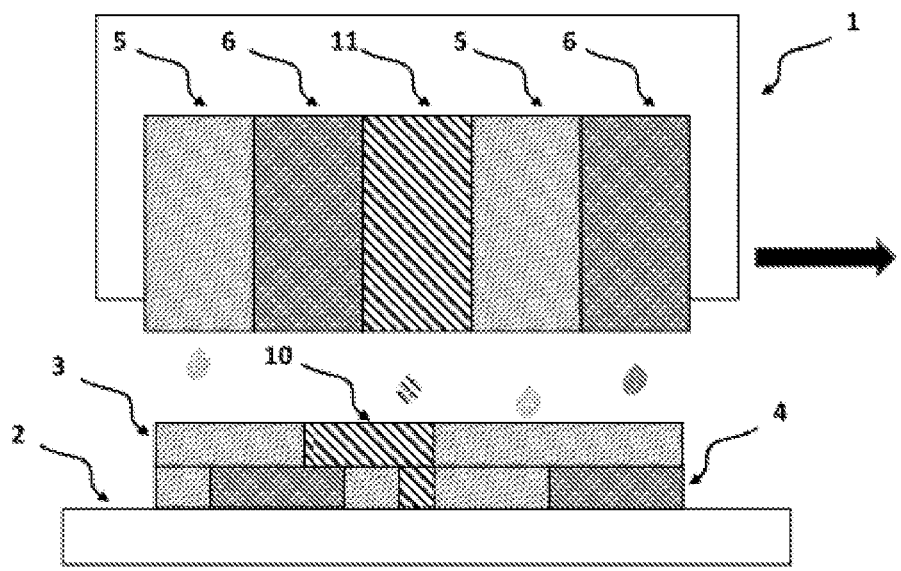
FIG. 4 shows a schematic representation of an additive manufacturing system according to the invention comprising a dyestuff-printer head and a multifold of ceramic component and support structure printer heads.

FIG. 4 shows a schematic representation of an additive manufacturing system according to the invention. The set-up is the same as described in FIG. 4. Nevertheless, in this Figure two sequentially deposited layers are depicted. It can be seen, that based on the position sensitive functionalization, different regions of the deposited ceramic component can be altered chemically by position sensitive deposition of the dyestuff 10.

Figure 5:
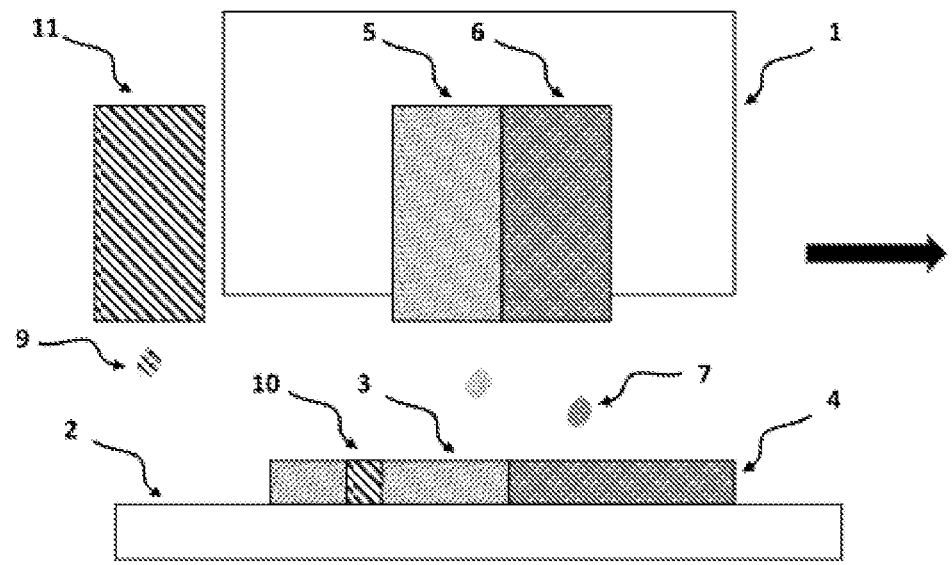
FIG. 5 shows a schematic representation of an additive manufacturing system according to the invention comprising a dyestuff-printer head separated from the ceramic component and support structure printer heads.

FIG. 5 shows a schematic representation of an additive manufacturing system according the invention. The system comprises a printer head 1 and the support structure 2. In contrast to the system in FIG. 3 the printer head 1 comprises only two different printer heads 5, 6, wherein the dyestuff printer head 11 is separated from the printer head for the support material 6 and the printer head for the ceramic component 5. Consequently, the printer head for the support material 6 deposits the support material 7, thereby forming regions of support material 4; the printer head for the ceramic component 5 deposits the ceramic component 8, thereby forming regions of ceramic component 3. The printer head for the dyestuff 11 deposits the dyestuff 9 onto the regions of the ceramic component 3 and thereby these regions of the ceramic component 3 are altered with respect to the chemical composition. Based on the dyestuff printer head 11 position the dyestuff 9 is applied to the already deposited ceramic component 3. Therefore, the dyestuff application can be better controlled, because the ceramic component could already settle in between the different deposition times. Based on the additive manufacturing process the dyestuff 9 can be placed very position and volume sensitive and allows a very precise tailoring of the color of the dental article. Furthermore, it is possible to achieve color gradients in one or more directions even in difficult geometries of the green body.

Figure 6:
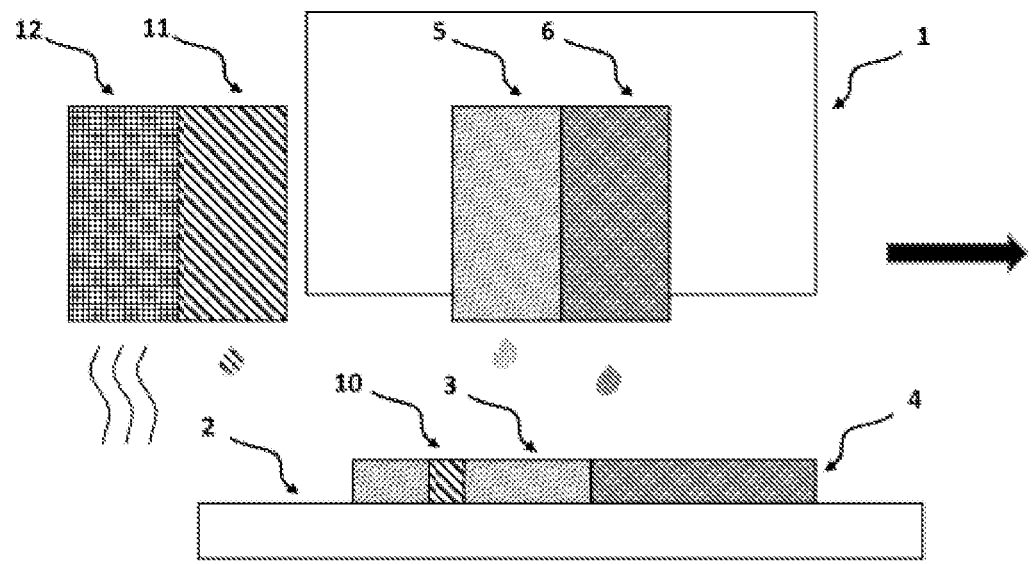
FIG. 6 shows a schematic representation of an additive manufacturing system according to the invention comprising a dyestuff-printer head and a separate position sensitive curing/heating device separated from the ceramic component and support structure printer heads.

FIG. 6 shows a schematic representation of an additive manufacturing system according the invention. The system comprises a printer head 1 and the support structure 2. Contrary to the system in FIG. 3 the printer head 1 comprises only two different printer heads 5, 6, wherein the dyestuff printer head 11 and an additional unit, a position sensitive curing/heating device 12, are separated from the printer head for the support material 6 and the printer head for the ceramic component 5. Consequently, the printer head for the support material 6 deposits the support material 7, thereby forming regions of support material 4; the printer head for the ceramic component 5 deposits the ceramic component 8, thereby forming regions of ceramic component 3. The printer head for the dyestuff 11 deposits the dyestuff 9 onto the regions of the ceramic component 3 and thereby these regions of the ceramic component 3 are altered with respect to the chemical composition. Based on the dyestuff printer head 11 position sensitive dyestuff 9 is applied to the already deposited ceramic component 3. Therefore, the dyestuff application can be better controlled, because the ceramic component could already settle in between the different deposition times. The position of the position sensitive curing/heating device 12 enables a direct change of the chemical surrounding directly after dyestuff deposition. This position allows a precise control of the penetration depth or the diffusion length of the dyestuff and can result in a higher position sensitivity compared to the state of the art systems. The position sensitive curing/heating device 12 may be a heating lamp, a laser or any other heat source capable of position sensitive curing/heating.

Figure 7:
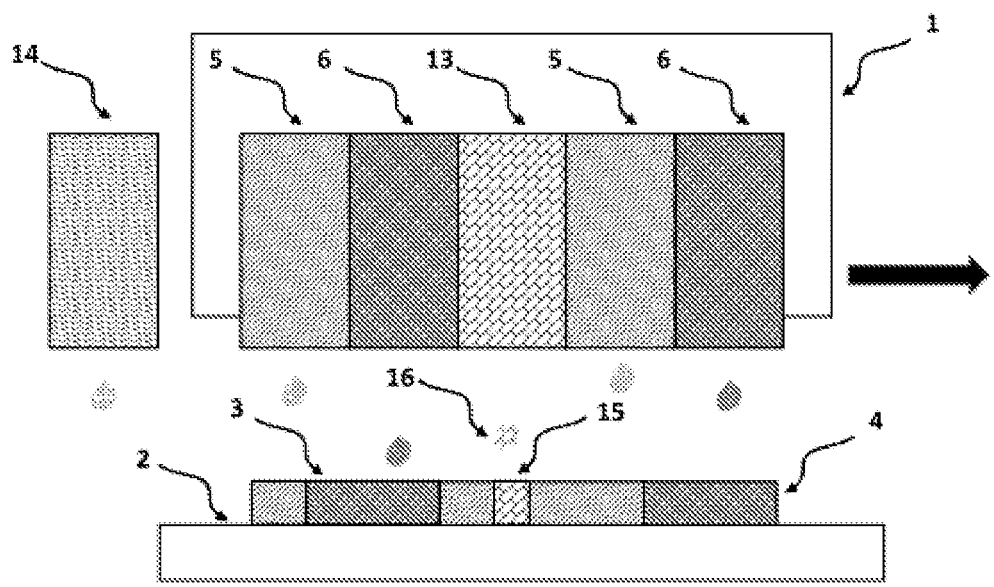
FIG. 7 shows a schematic representation of an additive manufacturing system according to the invention comprising a primer and developer-printer head.

FIG. 7 shows a schematic representation of an additive manufacturing system according the invention. This system comprises a set-up in principle comparable to FIG. 3. The system comprises a printer head 1 and the support structure 2. The printer head 1 comprises five different printer heads 5, 6, 13. Besides the two printer heads for the support material 6 and the two printer heads for the ceramic component 5 the printer head 1 comprises one printer head 13 for a primer solution. Consequently, the printer heads for the support material 6 deposit the support material 7, thereby forming regions of support material 4; the printer heads for the ceramic component 5 deposit the ceramic component 8, thereby forming regions of ceramic component 3. The printer head for the primer 13 deposits a primer solution or droplet 16 and not a dyestuff 9 onto the regions of the ceramic component 3 and thereby these regions of the ceramic component 3 are altered with respect to the chemical composition. The primer solution 16 is intended to form a dyestuff in combination with a developer, being deposited by the developer printer head 14. Only in case that primer 16 and developer are deposited on the same spot on the deposited surface 15, the color of the ceramic component is altered. Based on the position sensitive two-component deposition a finer gradation is achievable compared to a one spot dyestuff composition, only. The color change of the regions of ceramic component 3 may be immediately visible or the change may be achieved after an additional physical or chemical treatment of that region 15. Furthermore, by the two-component deposition it is possible to achieve more complex color gradients in one, two or three directions, even in difficult geometries of the green body. The doubling of the printer heads 5 for the ceramic component and the printer heads 6 for the support material enables a faster processing speed.

Figure 8:
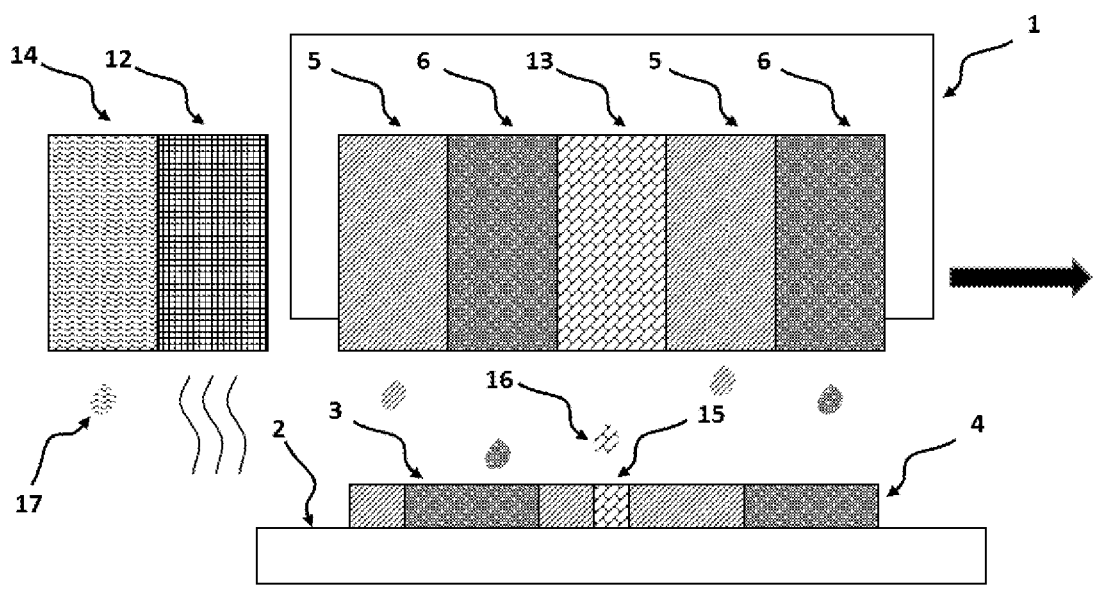
FIG. 8 shows a schematic representation of an additive manufacturing system according to the invention comprising a primer and developer-printer head and a position sensitive curing/heating device.

FIG. 8 shows a schematic representation of an additive manufacturing system according the invention. The system is similar to the system described in FIG. 7. In addition, the system comprises a position sensitive heating/curing device 12. Based on this device it is for instance possible, to selectively alter the chemical composition of the primer comprising surface 15. For instance, it is possible to evaporate a part of the primer solution 16 solvent, prior to applying the developer 17. Based on the triple position sensitive application, i.e. primer 16, heating/curing 12 and developer 17, it is possible to fine tune the spot color and the color gradation in multiple ways, enabling the processing and additive manufacturing of more natural looking dental ceramic articles.

LIST OF REFERENCE NUMERALS AND SIGNS

1 Printer Head
2 Support Structure
3 Deposited Ceramic Component
4 Deposited Support Material
5 Printer head Ceramic Component
6 Printer head Support Material
7 Support Material
8 Ceramic Component
9 Dyestuff
10 Deposited Dyestuff
11 Printer head Dyestuff
12 Position Sensitive Curing/Heating Device
13 Printer head Primer
14 Printer head Developer
15 Deposited Primer Solution
16 Primer
17 Developer solution

The invention claimed is:

1. A method for additive manufacturing of a position sensitive colored dental ceramic article comprising:
  a) providing at least one flowable ceramic component;
  b) forming a green body by sequential deposition of the flowable ceramic component provided in step a) and optionally a support material not intended to be part of a final article, wherein the flowable ceramic component is sequentially deposited in the form of particles dispersed in a dispersion medium;
  c) position sensitive application of a coloring substance in a solvent to at least a part of a surface of the green body being formed in step b), wherein the coloring substance is applied simultaneously to the sequential deposition;
  d) heat treatment or curing of at least a part of the green body surface obtained in step c);
wherein the method steps a)-d) are at least performed once;
  e) optionally removing the support material from the green body; and
  f) sintering the green body to obtain the ceramic article, wherein the coloring substance is a dyestuff according to ISO 18451-1:2019 (E); and
wherein the dispersion medium comprises $\geq 10$ wt. % and $\leq 40$ wt. % 2-(2-Butoxyethoxy)ethanol and the dispersed particles comprise $\geq 30$ wt. % and $\leq 60$ wt. % zirconium oxide, $\geq 0.001$ wt. % and $\leq 3$ wt. % hafnium oxide, $\geq 0.001$ wt. % and $\leq 8\%$ yttrium oxide; or,
wherein the dispersed particles comprise $\geq 2$ wt. % and $\leq 10$ wt. % yttrium oxide, $\geq 0.001$ wt. % and $\leq 10$ wt. % hafnium oxide, $\geq 0.001$ wt. % and $\leq 3$ wt. % aluminum oxide.

2. The method according to claim 1, wherein the dyestuff comprises a solubility in the solvent of step c) at 20° C. of $\geq 0.1$ g/l and $\leq 100.0$ g/l.

3. The method according to claim 1, wherein the dispersion medium is selected from the group consisting of water, ethanol, methanol, propanol, glycol derivates, butoxyethoxyethanol, butoxyethoxymethanol or mixtures of at least two components thereof.

4. The method according to claim 1, wherein the particles are selected from the group consisting of zirconium oxide, hafnium oxide, yttrium oxide, cerium oxide, aluminum oxide, or mixtures of at least two components thereof.

5. The method according to claim 1, wherein the particles are selected from the group consisting of silica-based glasses or mixtures thereof.

6. The method according to claim 1, wherein the dispersion medium is at least partially evaporated during at least one of step b) and d).

7. The method according to claim 1, wherein the heating or curing step d) is performed position sensitive.

8. The method according to claim 1, wherein the dispersion medium comprises a water content of $\geq 50$ wt. % and $\leq 100$ wt. %.

9. The method according to claim 1, wherein the heating or curing step d) also comprises a levelling treatment of the dried layer.

10. The method according to claim 1, wherein the coloring substance comprises a metal salt, wherein the metal salt comprises anions from the group consisting of $Cl^-$, $OAc^-$, $NO_3^-$, $NO_2^-$, $CO_3^{2-}$, $HCO_3^-$, $ONC^-$, $SCN^-$, $SO_4^{2-}$, $SO_3^{2-}$, lactate, fumarate or mixtures of at least two components thereof.

11. The method according to claim 1, wherein the coloring substance comprises a metal salt, wherein the metal salt comprises cations selected from the group consisting of Fe, La, Ce, Pr, Nd, Sm, Eu, Gd, Tb, Dy, Ho, Er, Tm, Yb, Lu, Mn, V, Cr, Ni or mixtures of at least two components thereof.

12. The method according to claim 1, wherein the solvent of the coloring substance in step c) is selected from the group consisting of glycol derivates, water, ethanol, methanol, propanol, butanol, butoxyethoxyethanol, butoxyethoxymethanol, tert-butyl methyl ether or mixtures of at least two components thereof.

13. Functionalized dental ceramic article obtained by a method according to claim 1.

* * * * *